(12) United States Patent
Baker (10) Patent No.: US 7,398,802 B2
(45) Date of Patent: Jul. 15, 2008

(54) SYSTEM FOR DISPENSING BIOLOGICAL FLUIDS

(76) Inventor: James W. Baker, 1055 SW. Englewood Dr., Lake Oswego, OR (US) 97034

( * ) Notice: Subject to any disclaimer, the term of this patent is extended or adjusted under 35 U.S.C. 154(b) by 682 days.

(21) Appl. No.: 10/933,849

(22) Filed: Sep. 2, 2004

(65) Prior Publication Data

US 2006/0049209 A1   Mar. 9, 2006

(51) Int. Cl.
B65B 1/04 (2006.01)

(52) U.S. Cl. .................. 141/27; 141/82; 141/319; 141/323; 141/330; 604/414; 604/415

(58) Field of Classification Search .............. 141/18, 141/21, 25–27, 82, 319, 323, 329, 330; 604/411–416
See application file for complete search history.

(56) References Cited

U.S. PATENT DOCUMENTS

| | | | | |
|---|---|---|---|---|
| 3,728,227 A | * | 4/1973 | Elson et al. | 435/287.3 |
| 3,835,897 A | * | 9/1974 | Gess | 141/98 |
| 3,935,883 A | * | 2/1976 | Stach et al. | 141/27 |
| 4,041,994 A | * | 8/1977 | Horwitz et al. | 141/1 |
| 5,555,920 A | * | 9/1996 | Godolphin et al. | 141/329 |
| 5,911,252 A | * | 6/1999 | Cassel | 141/234 |
| 6,877,530 B2 | | 4/2005 | Osborne et al. | |
| 6,976,349 B2 | | 12/2005 | Baldwin et al. | |
| 7,117,901 B2 | * | 10/2006 | Martinell Gisper-Sauch et al. | 141/2 |
| 2005/0281713 A1 | * | 12/2005 | Hampsch et al. | 422/102 |

* cited by examiner

Primary Examiner—Timothy L Maust
(74) Attorney, Agent, or Firm—Kolisch Hartwell, P.C.

(57) ABSTRACT

A method and apparatus for dispensing biological fluids. The system may provide supply (stock) vessels of refrigerated biological fluids that remain connected to dispensers as the dispensers are operated to distribute the biological fluids to receiver vessels. Each receiver vessel may be engaged selectively with a suitable set of one or more dispensers to select the type and amount of biological fluid to be dispensed to the receiver vessel. The dispensers may be configured to permit the biological fluids to be selectively dispensed to receiver vessels under sterile conditions, so that the biological fluids may remain in a substantially closed environment as they are transferred between vessels.

34 Claims, 5 Drawing Sheets

SYSTEM FOR DISPENSING BIOLOGICAL FLUIDS

An allergy is an untoward reaction of the body's immune system to a foreign substance. The foreign substance may be known as an allergen (an allergy generating substance) and/or an antigen (an antibody generating substance). The immune system is made up of two parts: the antibody-mediated system and the cell-mediated system. Allergic reactions to allergens have been classified into four major types (see Table 1). Three of these may involve the antibody-mediated system and one involves the cell-mediated system.

TABLE 1

Exemplary Types of Allergic Reactions

| Type | Immune System Involvement | Antigens (Allergens) | Exemplary Diseases |
|---|---|---|---|
| Type 1 | Immunoglobulin E (IgE) | Pets (dander), dust, mold, pollen, medications, venoms, foods | Allergic rhinitis, asthma, eczema, anaphylaxis, |
| Type 2 | Immunoglobulin G (IgG) | Drugs, other chemicals | Hemolytic anemia |
| Type 3 | Immunoglobulin G (IgG) | Drugs, other chemicals | Glomerulonephritis |
| Type 4 | Lymphocytes | Various chemicals | Contact dermatitis (poison ivy) |

In the case of type 1 mediated allergy, allergens such as animal (pet) dander, dust mite antigen, mold, and/or pollen may combine with IgE antibodies on the surface of white blood cells known as mast cells. These cells then may secrete a number of chemicals including histamine which may cause hives, itchy watery eyes, nasal congestion, nasal discharge, throat swelling, coughing, wheezing, shortness of breath, gastrointestinal symptoms, and/or a shock-like state. A medical history and a physical from a patient with allergy symptoms may be used by a practitioner to make a presumptive diagnosis of type 1 mediated allergic disease. This diagnosis may be confirmed with skin tests and/or blood tests (RAST test) to test for the presence of antigen-specific IgE.

Management of allergic disease involves three major strategies: avoidance of the allergen, medications to block the allergic reaction, and/or immunotherapy. Of these, immunotherapy may be the most practical and effective, because it involves long-term desensitization to particular allergens by systemic exposure to controlled levels of these allergens. Immunotherapy involves making a vaccine from the various allergen extracts to which a patient is sensitive. The vaccine may be prepared by mixing the extracts in a vial. For example, the patient might have positive skin tests to extracts from tree pollen, grass pollen, and cat dander. The vaccine may be prepared as a mixture of these extracts in a vial and then diluted to a level that the patient can tolerate for injection. Immunotherapy generally involves injection of increasing doses (decreasing dilutions) of the mixture over time, such as over the course of months or years, to a level that may be much higher than (in some cases several orders of magnitude greater than) the initial dose. This approach decreases the sensitivity of the patient to the injected mixture (and thus the injected allergens) and hopefully helps control the underlying allergic disease.

At present, most practitioners mix extracts using individual syringes to transfer specific amounts and concentrations of extracts from stock bottles to the patient's vial. Since the allergen mixture, or a dilution thereof, may be injected into the patient, the desired allergens/extracts generally are combined in the patient's vial under sterile conditions.

FIG. 1 shows a series of configurations produced by performance of a common method 20 for sterile transfer of a selected allergen 22. The allergen 22 may be provided as a sterile extract in liquid, contained in a stock vial 24. The stock vial may be generally transparent and may be sealed at its mouth with a closure 26, such as a resilient septum 28. Septum 28 may be held in place by a retainer 30 extending around the neck of the vial 24, and particularly around a collar or flange formed on the neck of the vial. Retainer 30 also may extend partially over the exterior surface of the septum to leave an exposed region 32 of the septum for access to interior of the vial with a hollow-bore needle. The allergen 22 may be transferred to a patient's vial 34, which may be of generally similar construction to the stock vial, but often smaller in size. Transfer may be performed with a syringe 36 having a barrel 38 with graduations for volume measurement and a hollow-bore needle 40 for penetration of the septum 28.

Configuration 42 shows stock vial 24 prepared to receive the needle 40 of the syringe. The stock vial 24 may be in an upright or inverted configuration. The exposed region 32 of the septum and the exterior surface of the needle may need to be sterilized. Accordingly, the exterior surface of the septum may be sterilized by wiping this surface with alcohol prior to penetration with the needle, and the needle may be obtained in a sterile condition, such as by treatment with heat, steam, a chemical, high-energy particles, and/or electromagnetic radiation, among others. Furthermore, the stock vial, the syringe, and the patient's vial may be disposed in a laminar flow hood equipped with bacteriostatic illumination before, during, and/or after performance of the steps illustrated in FIG. 1.

Configuration 44 shows stock vial 24 placed in fluid communication with syringe 36 by insertion of the needle through the septum and into contact with the allergen. The plunger 46 of the syringe has been withdrawn from the barrel to load a measured volume of the allergen, shown at 47, from the stock vial into the barrel 38.

Configuration 48 shows syringe 36 removed from the stock vial with the measured volume 47 of the allergen and positioned above the patient's vial 34. The patient's vial also may need to be sterilized (or re-sterilized) on the exterior surface where the syringe will penetrate the septum 50, particularly if the patient's vial has already received other allergens in separate dispensing operations.

Configuration 52 shows syringe 36 placed in fluid communication with the patient's vial by penetration of the septum of the patient's vial with the needle 40 of the syringe. Plunger 46 may be pushed into the barrel 38 of the syringe to expel the measured volume of the allergen from the syringe barrel into the patient's vial.

The method shown here may be repeated for each selected extract to introduce a desired set and ratio of allergens into the patient's vial and thus to form a custom mixture for further dilution and/or injection into a patient. However, this commonly used method for preparation of allergen mixtures may have a number of drawbacks. Generally, each stock vial may be placed at room temperature from refrigerated storage, and allowed to remain at room temperature and exposed to light before and during formation of allergen mixtures. In some cases, the stock vials may sit at room temperature, exposed to light, for many hours as various allergen mixtures are being prepared. Over time, the allergens in the stock vials thus may be physically and/or chemically damaged (such as denaturation, oxidation, and/or cleavage of allergen proteins), with unpredictable changes in allergen potency that may affect diagnosis or treatment of patients using the allergens. Furthermore, this common method of preparing allergen mixtures may be too labor intensive, wasteful of syringes, unsafe, and/or prone to contamination and/or human error, among others.

SUMMARY

The present teachings provide systems, including methods and apparatus, for dispensing biological fluids, such as allergens.

DETAILED DESCRIPTION

The present teachings provide systems, including methods and apparatus, for dispensing biological fluids. The systems may provide supply (stock) vessels of biological fluids that remain connected to dispensers as the dispensers are operated to distribute the biological fluids to receiver vessels. Each receiver vessel may be engaged selectively with a suitable set of one or more dispensers to select the type and amount of biological fluid to be dispensed to the receiver vessel. The dispensers may be configured to permit the biological fluids to be selectively dispensed to receiver vessels under sterile conditions, so that the biological fluids may remain in a substantially closed environment as they are transferred between vessels.

Further aspects of the present teachings are included in the following sections, including, among others, (I) overview of an exemplary dispensing system, (II) vessels, (III) biological fluids, (IV) dispensers, (V) housings, (VI) controllers, (VII) methods of operation, and (VIII) examples.

I. Overview of an Exemplary Dispensing System

Figure 1:
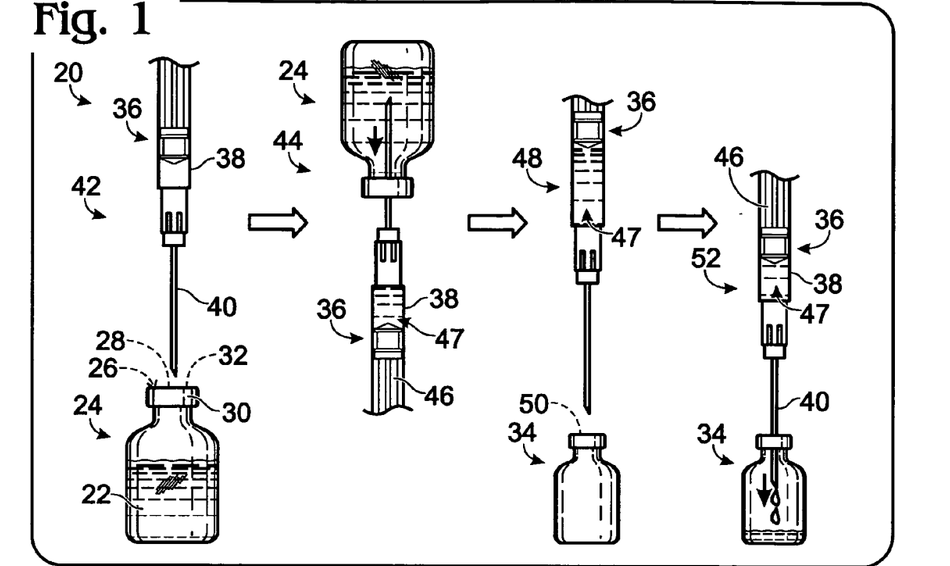
FIG. 1 is a series of configurations produced by performance of a common method for sterile transfer of an allergen extract from a stock vial to a patient's vial so that a customized mixture of allergens can be prepared for further dilution and/or injection into a patient.
Figure 2:
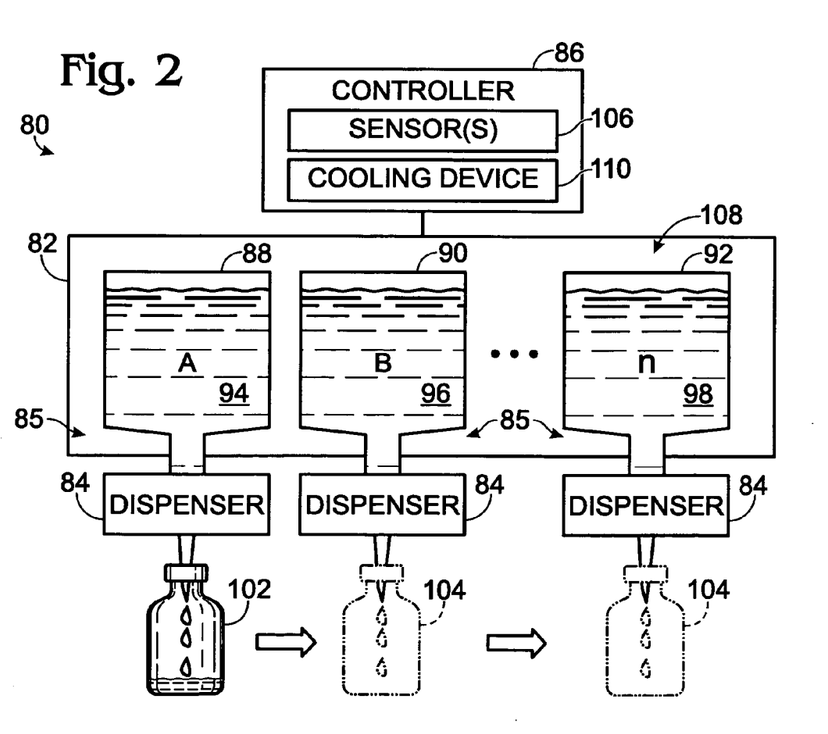
FIG. 2 is a schematic view of an exemplary system for dispensing biological fluids, in accordance with aspects of the present teachings.

FIG. 2 shows a schematic view of an exemplary system 80 for dispensing biological fluids, such as allergens, in accordance with aspects of the present teachings. System 80 may include a housing 82, a plurality of dispenser units 84 coupled to the housing, and a controller 86 to monitor and/or regulate any suitable aspects of the system.

Housing 82 may be configured to hold a plurality of supply (stock) vessels, such as vessels 88, 90, 92. Each stock vessel may include a biological fluid, such as fluids 94, 96, 98, generally in liquid form. The housing may be configured to protect the supply vessels and their biological fluids from ambient conditions, for example, by defining an interior compartment that may be cooled, protected from light, etc. In some examples, the housing may be coupled movably to a base, so that the housing may reciprocate or turn, among others, on the base. This movement of the housing may permit a person dispensing the biological fluids to gain sequential access to, and/or to conveniently position, different dispensers/biological fluids.

Dispenser units (or dispensers) 84 each may be configured to remain coupled continuously to the housing and to the supply vessels during dispensing operations and/or when system 80 is idle, to provide a set of dispenser stations 85. Accordingly, the dispensers (and the dispenser stations) may be attached to the housing with fixed relative positions, so that the dispensers are disposed in a fixed array for more convenient and/or error-free identification of dispenser stations. The dispensers/dispenser stations also may be configured to be uncoupled from the housing (with or without their coupled supply vessels) to permit, for example, maintenance, replacement, and/or replenishment of dispensers, supply vessels, and/or biological fluids. The dispensers may be coupled to a receiver vessel 102 into which one or more of the biological fluids may be dispensed. The receiver vessel 102, shown in solid outline, may be coupled to only one dispenser, or may be coupled in parallel or sequentially to one or more additional dispensers, shown in phantom outline at 104.

Figure 3:
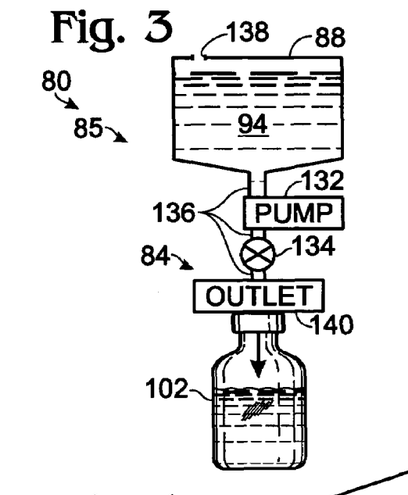
FIG. 3 is a somewhat schematic view of a dispenser station from the system of FIG. 2.

Controller 86 may be coupled to the housing, the supply vessels, and/or the dispensers, among others. The controller may include one or more sensors 106 to detect one or more aspects of the system, such as the temperature and/or humidity of an interior compartment 108 the housing, among others. The controller also or alternatively may include one or more devices for modifying a condition of the interior compartment, such as a cooling device 110 and/or humidifier/dehumidifier, or the like. The controller further may be in communication with the dispensers to monitor and/or regulate aspects of dispenser operation, such as selective actuation of individual dispensers.

FIG. 3 shows a somewhat schematic view of a dispenser station 85 from system 80. The dispenser station, and particularly the dispenser unit 84 of the station, may include a pump 132 to move fluid, and a valve 134 operable to direct and/or restrict fluid flow through a conduit structure 136 of the dispenser unit. The conduit structure may provide fluid communication between the supply vessel 88, the pump, the valve, and/or the receiver vessel 102.

In some examples, operation of the valve may place the dispenser unit in a loading configuration or in a delivery (or release) configuration. The loading configuration may place the pump in fluid communication with the biological fluid 94 of the supply vessel 88, for loading a measured volume of the biological fluid into the pump. The supply vessel also may include or be coupled to a vent 138 that restricts formation of a negative pressure in the supply vessel during loading. The delivery configuration may place the pump in fluid communication with an outlet 140 that may be coupled to a receiver vessel 102, for delivering the measured volume to the receiver vessel with the pump. The pump and/or the valve may be operated manually and/or automatically. In some examples, the valve may be operated by moving the pump between a loading configuration and a release configuration. In other examples, the valve further may be operated by moving the pump between additional configurations, such as two or more loading configurations, two or more release configurations, holding configurations, and so on.

The systems provided herein may have a number of advantages for dispensing biological fluids, particularly forming mixtures of allergens for immunotherapy. The advantages may include one or more of the following, among others: (1) reduced light-mediated degradation of biological fluids, (2) reduced temperature-mediated degradation of biological fluids, (3) increased speed of dispensing to form mixtures, (4) decreased labor costs, (5) fewer punctures of stock vessels (through their closures) and thus a reduced number of closure-derived plugs in the biological fluids, (5) improved longevity and consistency of biological fluids, (6) improved organization of stock biological fluids in an array, (7) reduced chance of needle sticks, (8) reduced repetitive finger injuries, (9) decreased chance of errors in dispensing, (10) reduced chance of replacing syringe needle in wrong stock vessel, (11) reduced repetitive sterilization of closures of stock and receiver vessels (and associated chance of sample contamination and/or degradation), (12) reduced set-up time, (13) easier replacement of stock vessels when depleted, (14) higher speed without the expense and maintenance costs of a high technology system, (15) parts may be disposable, (16) decreased syringe usage, (17) vented with reduced vacuum, less denaturation, and fewer air bubbles than would be produced typically by fast movement of fluid through needles, (18) quicker and/or more efficient addition of diluent, (19) definite procedure for loading, checking, and delivering to increase accuracy, (20) reduced need for bacteriostatic lights (which may denature allergens), (21) reduced chance of contamination, (22) less chance of undesired direct contact between fluids in stock and receiver vessels, (23) manual operation that is easy to learn, and/or (24) reduced condensation and thus fewer problems with labels coming off vessels.

II. Vessels

The dispensing systems described herein may be configured to be used with vessels for holding biological fluids. The vessels may have any suitable size, shape, composition, closure, and/or coupling structure, among others.

The size of each vessel may be selected, for example, according to the volume of biological fluid(s) to be held in the vessel, the capacity of the pump, and/or the volumes to be dispensed, among others. Accordingly, supply vessels may be large enough to hold one dispensed volume or a plurality of dispensed volumes. In some examples, the supply vessels may be large enough to hold many dispensed volumes, such as about 10, 100, or 1,000 dispensed volumes, among others. In some examples, each dispensed volume may be about 0.1 to 1.0 milliliters and a supply vessel may have a capacity of about 10 to 100 milliliters of fluid. In other examples, the supply vessel may have a capacity of about 0.1 to 10,000 milliliters. Similarly, receiver vessels may be large enough to hold at least one dispensed volume or a plurality of dispensed volumes, with or without added diluent. Receiver vessels thus may be similar in size to supply vessels, or larger or smaller than the receiver vessels. In some examples, a receiver vessel may have a capacity of about 5 to 25 milliliters. In other examples, the receiver vessel may have a capacity of about 0.1 to 1000 milliliters.

The vessels may be shaped according to their intended purposes. The vessels may be generally cylindrical, frusto-conical, spherical, cubical, polyhedral, and/or the like. The vessels may have flat bottoms, to support the vessels on a flat surface. The vessels may a varying diameter, for example, narrowing near the top of the vessels, to provide a neck that defines the mouth of the vessels.

The vessels may be formed of a material that is generally inert to the biological fluids. Exemplary materials may include glass, plastic, and/or metal, among others. The material may be at least partially transparent. The material may be colorless, or may be colored, for example, darkened or tinted to restrict entry of light.

The vessels may have closures to seal the vessels. A closure may be any structure that at least substantially restricts passage of fluid, and particularly a liquid, into and/or out of a vessel. The closures may include plugs, septa, caps, lids, and/or the like. Closures may be secured to vessels by threadable engagement, an interference fit, a clip or retainer, a resilient flange, and/or the like. In some examples, the closures may be configured to receive a conduit, such as a hollow-bore needle that penetrates the closures. Accordingly, the closures may be resilient, for example, formed of plastic and/or rubber, and/or may include a preformed aperture to receive the conduit.

The vessels may include coupling structures to permit conduits to be coupled to the vessels. The coupling structures may be included in the closures, and/or may be distinct from the closures. The coupling structures may permit conduits to be placed in fluid communication with the vessels in a sealed relationship, so that fluid can pass through the conduits from and/or to vessels, but generally not adjacent the exterior of the conduit.

In exemplary embodiments, the vessels may be vials. A vial, as used herein, is a closed vessel for holding small amounts of fluid, generally less than about 100 milliliters. The vials may include resilient closures, such as septa, that restrict fluid passage from/to the vials. The closures may be penetrated by conduits, such as hollow needles, to permit fluid movement from/to the vessels, for example, to remove and/or add a volume of biological fluid to/from the vessels and/or to function as a vent during and/or after this movement. Resiliency of the closures may provide a seal around the conduits after the closures are penetrated by the conduits.

III. Biological Fluids

The dispensing systems described herein may be configured to be used for transfer of biological fluids between vessels, particularly for forming predefined mixtures of the biological fluids in vessels.

The biological fluids generally include any fluid—liquid and/or gas—at least partially derived from and/or affecting living organisms. The biological fluids may include any suitable ratios of biological extracts, synthetic compounds, microorganisms, organelles, excipients, diluents, buffers, salts, and/or the like. The biological fluids also may include markers, such as dyes and/or other (preferably biologically inert) compounds, to identify the fluid and/or to indicate addition or removal of fluids during sample preparation. The biological fluids may be aqueous, or predominantly aqueous, having water as a major component. However, in some cases, the fluids may be organic, having an organic solvent (particularly a biologically compatible organic solvent such as DMSO or DMF) as a major component. Alternatively, or in addition, the biological fluids may include trace amounts of organic solvents, such as DMSO or DMF, particularly if used as a carrier for another component.

The biological fluids may be used for any suitable purpose. For example, each biological fluid may be a preparation, such as a drug, a vaccine, or an antitoxin, used medically as a diagnostic, preventive, and/or therapeutic agent. The preparation may be at least partially synthesized by living organisms or their products, and/or may be based structurally on a material produced by a living organism. Exemplary biologically active agents in biological fluids may include proteins, peptides, nucleic acids, carbohydrates, vitamins, metal ions, lipids, hormones, etc. More specifically, exemplary biologically active agents may include allergens, such as extracts (particularly protein extracts) from food, molds, animal dander, plants, pollens, dust mites, venoms, bacteria, and/or the like. In some examples, the biological fluids may include synthetic allergens, for example, synthetic peptides. Exemplary biologically active agents also may include research, diagnostic, and/or clinical materials obtained via any suitable mechanism (e.g., excisions, aspirations, swipes, swabs, phlebotomies, etc.) from biopsies and/or necropsies of cells, tissues, and/or biological fluids (e.g., saliva, blood, urine, lymph, mucous, semen, etc.), among others.

The biologically active agents may be present at any suitable concentration. Accordingly, in some examples, the biological fluids may include different dilutions of a biologically active agent, such as serial two-fold or ten-fold dilutions, among others. Alternatively, or in addition, the biological fluids may include repetitions of the same fluid (i.e., two or more stations having the same fluid), particularly commonly used fluids.

The biologically active agents may be present in any suitable amount(s), in any suitable state(s). The amounts may be measured by concentration, for example, picomolar, nanomolar, micromolar, millimolar, and molar. Alternatively, or in addition, the amounts may be measured in effective amounts, for example, effective to induce or desensitize an immune response, effective to bring about a desired therapeutic response, effective to diagnose a condition, and so on. The suitable states may include solutions, suspensions, emulsions, dispersions (including colloidal dispersions), gels, aerosols, and so on, and/or mixtures thereof.

IV. Dispensers

The dispensing systems described herein may include one or more dispenser stations at which biological fluids may be dispensed. Each dispenser station may include a dispenser configured for manual and/or automatic operation and may include at least one pump, valve, and/or outlet, and suitable conduits providing fluid communication between these structures. The dispenser stations optionally may include or share a dispenser housing, in which some or all of the other dispenser components are supported, protected, and/or connected. In some cases, the dispenser station at a given position may be missing, replaced with a nonfunctional blank, or replaced with a solid dispenser (e.g., to dispense easily soluble materials such as salts for use in preparing buffers). In the same or other cases, dispensers designated for and/or containing biological fluids related by some common characteristic (e.g., type (e.g., grass allergen, tree allergen, etc.), concentration (e.g., low concentration, high concentration, etc.), and so on) may be organized relative to one another according to some predefined criteria or rule. For example, biological fluids that commonly would be dispensed into a common receiving vessel may be positioned adjacent one another to enhance the speed and convenience of dispensing, and biological fluids that less commonly would be dispensed together, or that should not be dispensed together, may be positioned far from one another to reduce the possibility that they will be co-dispensed.

A. Pumps

Pumps generally include any device for actively moving biological fluids within the dispensers. Such active movement may be effected by pushing and/or pulling and/or otherwise biasing fluid to and/or from the pumps. The active movement may be effected, for example, by directly pushing on the fluid, for example, by a piston, a vane, pressurized gas, and/or a spring, among others.

Pumps used for dispensing may be any suitable manual- or power-driven pumps. The pumps may be positive-displacement and/or dynamic pumps, among others. Positive-displacement pumps may move fluid by filling a cavity and then displacing a given volume of the fluid. Exemplary positive-displacement pumps may include piston, bellows, double-diaphragm, flexible impeller, gear, oscillating, progressing cavity, rotary, and/or peristaltic pumps, among others. Dynamic pumps may move fluid by increasing its speed or velocity. Exemplary dynamic pumps may include centrifugal pumps. Power-driven pumps may be operated manually, such as by having a user or operator manipulate pump controls (buttons, switches, levers, etc.), and/or automatically, such as with an electronic controller. The pumps may be configured to move measured volumes of fluid, for example, based on the number of pump strokes/cycles performed, and/or based on the size of a partial stroke/cycle of a pump, among others. Any suitable volume may be measured and moved by a pump.

Exemplary pumps may include manually-driven or power-driven syringe pumps. The syringe pumps may have any suitable barrel capacity, such as a capacity of about 0.1 to 10 milliliters, among others. In some examples, a dispensing system may include syringes of different capacities coupled to different dispensers, such as smaller capacity syringes for dispensing allergens and larger capacity syringes for dispensing excipients/diluents. In exemplary embodiments, some or all of the syringe pumps may have a capacity of about one milliliter. Graduations or other indicia on the syringe pumps may be used to set and/or permit visual measurement of loaded/delivered fluid volumes.

B. Valves

Valves generally include any device for controlling the velocity (including the starting and stopping) and/or direction of flow of biological fluids within the dispensers. The valves may be operated manually, with or without power-driven assistance (such as a solenoid operated by a switch), and/or automatically (such as with an electronic controller and a solenoid). Exemplary valves may include angle, ball, butterfly, diaphragm, gate, globe, needle, pinch, and/or stop cock valves, among others. Exemplary valves alternatively and/or in addition may include two-way, three-way, four-way, and/or higher-order way valves, capable of receiving and/or directing fluid from any suitable or desired directions, and/or numbers of directions.

C. Outlets

Outlets generally include any structures at which biological fluids can be delivered from dispensers to receiver vessels. The outlets thus may include a conduit having a tip from which the biological fluids may be released. The tip may be blunt or sharp (such as a hollow-bore needle). Outlets may include coupling structure with which the outlet conduit may be coupled to a receiver vessel, such as a plug, cap, and/or the like, attached to the outlet conduit and configured for engagement with the receiver vessel. This plug or cap may be sealed circumferentially around the outlet conduit to restrict fluid leakage. Alternatively, the outlet conduit itself may engage the receiver vessel so that the conduit is sealed against the vessel, such as by penetration of a closure of the receiver vessel, or the outlet conduit may deliver biological fluids in a nonsealed relation with the receiver vessel (such as through an open mouth of this vessel). The outlet may be configured for contact and/or noncontact dispensing (in which the outlet contacts or does not contact the receiving fluid or container as part of the dispensing process, respectively).

D. Conduits

The dispensers may include conduits that provide fluid communication between the valve, pump, supply vessel, and/or outlet. The conduits may include any suitable mechanism for routing fluid, such as rigid tubes, flexible tubing, and/or the like.

E. Dispenser Housing

The dispensers also may include a dispenser housing to which a pump, a valve, and/or an outlet may be connected. The dispenser housing may include coupling structure that permits attachment of the dispenser to the dispensing system. The dispenser housing also may have a number of other functions (such as guiding/restricting operation of the pump and/or valve; and/or protection of the conduits, pump, valve, and/or outlet from contamination, damage, inadvertent uncoupling, etc.; among others). Accordingly, the dispenser housing may include any suitable number of openings to permit access to the outlet, pump, and/or valve, and/or to permit conduits to extend from the dispenser housing. The dispenser housing also may support a supply vessel of biological fluid, for example, by receiving the supply vessel in an opening defined by the dispenser housing.

The dispenser housing, another portion of the dispenser station, and/or the associated system housing may include indicia that identifies the biological fluid dispensed by the dispenser station. The indicia may include one or more alphanumeric characters (such as letters, words, and/or numbers), symbols, pictures, a color code, a bar code, an electronic code (such as data on a readable electronic chip), and/or the like. These indicia may be used to verify and/or track the type of material (biological material) associated with the dispenser, before and/or after dispensing. In some cases, the indicia may be removable (such as one or more preprinted or custom printed stickers) and/or scanable (such as by an optical reader) to facilitate compiling a record of dispensed materials.

V. Housings

The dispensing systems described herein may include one or more housings to hold dispenser stations and their supply vessels. Each housing may protect the supply vessels from ambient conditions and/or may organize and/or adjustably position the dispenser stations (and/or their supply vessels and/or dispensers), among others.

The housing may have suitable size and shape. The housing may be large enough to hold any suitable number of dispensers and supply vessels. Portions of the dispensers (such as the housings, pumps, valves, and/or outlets) may be disposed substantially outside (or substantially inside) the housing. The housing may hold the supply vessels substantially (or completely) in an interior compartment defined by the housing. The interior compartment may be a chamber that can be substantially closed to the outside. The housing may be generally circular (or cylindrical), polygonal, rectangular, and/or the like.

The housing may define a plurality of openings. At least a subset of the openings may be configured to receive supply vessels, conduits, and/or portions of the dispensers. The openings may be disposed adjacent the lateral walls of the housing, so that the supply vessels and dispensers are positioned around a central axis of the housing. Alternatively, the openings may be disposed in one row or in a plurality of generally parallel rows. In some examples, openings of the housing that are not in use may be covered with a plug or a cap, among others, to restrict air flow through these openings. In some examples, one or more openings of the housing may be configured to receive a cooling device, electrical or fluid conduits, and/or the like.

The housing may be fixed or movable relative to a support structure (such as a coupled base) that supports the housing. A fixed housing may be mounted fixedly on the support structure, for example, a housing with legs affixed to the housing. A movable housing may be coupled to a support structure so that the housing and its connected dispensers can be moved in relation to the support structure and in relation to a person operating the dispensers. The housing may move rotationally (e.g., turn) and/or translationally (e.g., slide). Translational movement may include linear reciprocation and/or orthogonal movement, among others. In some examples, only a portion of the housing may be movable, such as a portion connected to a subset (or all) of the dispensers.

The housing may have any suitable composition. In some examples, the housing may be formed at least partially of a substantially transparent material, so that the interior compartment of the housing and its contents may be examined visually from external the compartment. In some examples, the side walls of the housing may be transparent. In some examples, the housing may be configured to restrict entry of light into the housing. Accordingly, the housing may include one or more transparent, colored or darkened walls, and/or one or more opaque walls. These materials may be selected according to any suitable criteria, e.g., to be biologically inert, easy to clean, difficult to break, and so on.

VI. Controllers

The dispensing systems described herein may include one or more controllers. Each controller may be configured to monitor and/or control aspects of operation of a dispensing system.

The controller may include a user interface. The user interface (such as a mouse, joystick, keyboard, keypad, buttons, switches, touchscreen, etc.) may permit a user to input data, such as instructions and/or preferences for dispensing. The user interface alternatively or additionally may include a screen, one or more indicator lights, etc., to output instructions, progress indicators, and/or data, among others, to the user, such as a record of dispensing operations, status reports, warnings, etc.

The controller may include digital instructions and processing capabilities. For example, the controller may include a processor to perform data manipulation. The controller also or alternatively may include a memory to store instructions that may be used by the processor.

The controller may include one or more sensors configured to sense any suitable aspects of a dispensing system. Such aspects may include temperature, light intensity, humidity, gas composition, position of the housing, fluid levels in supply vessels, pump positions, valve positions, and/or the like. Such aspects also may include the types and/or volumes of fluids dispensed, the timing and/or order of the dispensing, and so on. The controller may store and/or facilitate display and/or output of sensed aspects, for example, to maintain a record of the sample and sample preparation.

The controller may include or may be connected to one or more power-driven devices. Alternatively, these devices may operate independent of a controller. Such devices may include positioners/drivers for movement/operation of the housing, pumps, valves, supply vessels, outlets, and/or the like. Such devices alternatively or additionally may include environmental modifying devices, such as heaters, coolers, light sources, gas sources, etc. These devices may receive and/or be controlled in response to sensed aspects of the system, such as temperature, as described above. In some examples, the controller and/or the dispensing system may include a thermoelectric cooling device that operates according to the Peltier effect. Such a thermoelectric cooling device may reduce condensation while refrigerating the interior compartment of the housing, and the supply vessels and their contents, thereby minimizing damage to, and/or detachment of, labels, and/or growth of microorganisms, among others.

VII. Methods of Operation

The dispensing systems described herein may be suitable for performing methods of dispensing biological fluids, particularly to form mixtures of the fluids. In some examples, the biological fluids may be allergens, that is, allergen extracts or synthetic allergen compounds at any suitable dilution. The methods may include any suitable combination of the following steps, or other steps, performed any suitable number of times, and in any suitable order. These steps may be planned and selected before and/or during dispensing. In some cases, the steps (including the types and/or amounts of fluids dispensed) may be determined by stand-alone and/or associated software. Such software-determined steps may be provided in any suitable format, such as a printout, a series of software prompts, and so on.

A single biological fluid or a mixture of biological fluids to be prepared may be identified or selected. In some examples, the mixture may be defined based on allergen sensitivity testing. Identification or selection of the mixture may identify or select a set of biological fluids to be included in the mixture and volumes/dilutions/concentrations for each fluid of the set (or for a single fluid). This step of identification or selection also may select a volume(s) of diluent(s) and/or excipient(s) to be included in the mixture (or to be combined with the single biological fluid).

A dispensing apparatus may be selected and readied for operation. In particular, supply vessels holding the biological fluids of the set (and, optionally, supply vessels holding other biological fluid that are not in the set) may be connected to dispensers of the dispensing apparatus. The supply vessels may be disposed in a refrigerated compartment of the dispensing apparatus and may be protected from light.

One of the fluids of the set may be selected. Selection may include a step of moving a dispenser (connected to a supply vessel holding the fluid selected), so that the dispenser is more conveniently positioned relative to a person operating the dispensing apparatus. The step of moving may include turning, and/or inducing translational motion of, a housing to which the dispenser is connected.

A measured volume of the selected fluid may be transferred from its supply vessel to a receiver vessel. The step of transferring may be performed by passing a portion of the selected fluid through a closure of the supply vessel and/or the receiver vessel, and may be performed with the supply vessel continuously connected to its dispenser. Accordingly, the step of transferring may be performed as the measured volume remains within a substantially closed environment, under sterile conditions.

The step of transferring may include a step of loading a pump with a biological fluid and a step of delivering the biological fluid from the pump to a receiver vessel. In some examples, the step of loading a pump may be performed by placing the pump in fluid communication with a supply vessel connected to the pump, and then operating the pump to draw a portion of the fluid into the pump. The pump may be used to load a predefined volume that is substantially delivered to the receiver vessel. Alternatively, the pump may be used to load a volume that is larger than the volume delivered to the receiver vessel, so that only a portion of the loaded volume is delivered. In some examples, the step of delivering the biological fluid may include a step of placing the pump in fluid communication with a receiver vessel and/or a step of operating the pump to release biological fluid to the receiver vessel. In each case, the step of placing the pump and/or the step of operating the pump may be performed manually or automatically.

Additional biological fluids of the set may also be selected and transferred. Transfer with different dispensers to the same receiver vessel may be performed at different times (generally, sequentially) or at the same time (for example, by providing two or more outlets with tubing long enough to reach the receiver vessel at the same time).

VIII. Examples

The following examples describes selected aspects and embodiments of the present teachings, including an exemplary dispensing apparatus for creating an allergen mixture for immunotherapy by transferring measured volumes of allergen stocks from stock vials to a patient's vial under sterile conditions; see FIGS. 4-14. These examples and the various features and aspects thereof are included for illustration and are not intended to define or limit the entire scope of the present teachings.

FIG. 4 show an exemplary apparatus 180 for preparing mixtures of allergens and/or other biological fluids. The apparatus may include a housing 182, a base 184, and a plurality of dispenser stations 186, among others.

The housing 182 may be coupled pivotably to a base 184 so that the housing can turn around pivot axis 188. Accordingly, the housing may function as a carousel to provide adjustable access to allergen stocks 190 disposed in an interior compartment 192 defined by the walls of the housing. The base may include legs 194 mounted on, and extending upwardly from, a platform 196.

The housing may include any suitable structure. For example, the housing may include a bottom wall 198, a top wall 200, and a plurality of side walls 202 extending between the bottom and top walls. The bottom and top walls may be opaque or transparent, and the side walls may be transparent, and may be darkened to restrict access of light. Accordingly, the side walls may be formed of plastic and/or glass, and other portions of the housing may be formed of any suitable material including plastic, metal, composite, glass, and/or the like.

Figure 4:
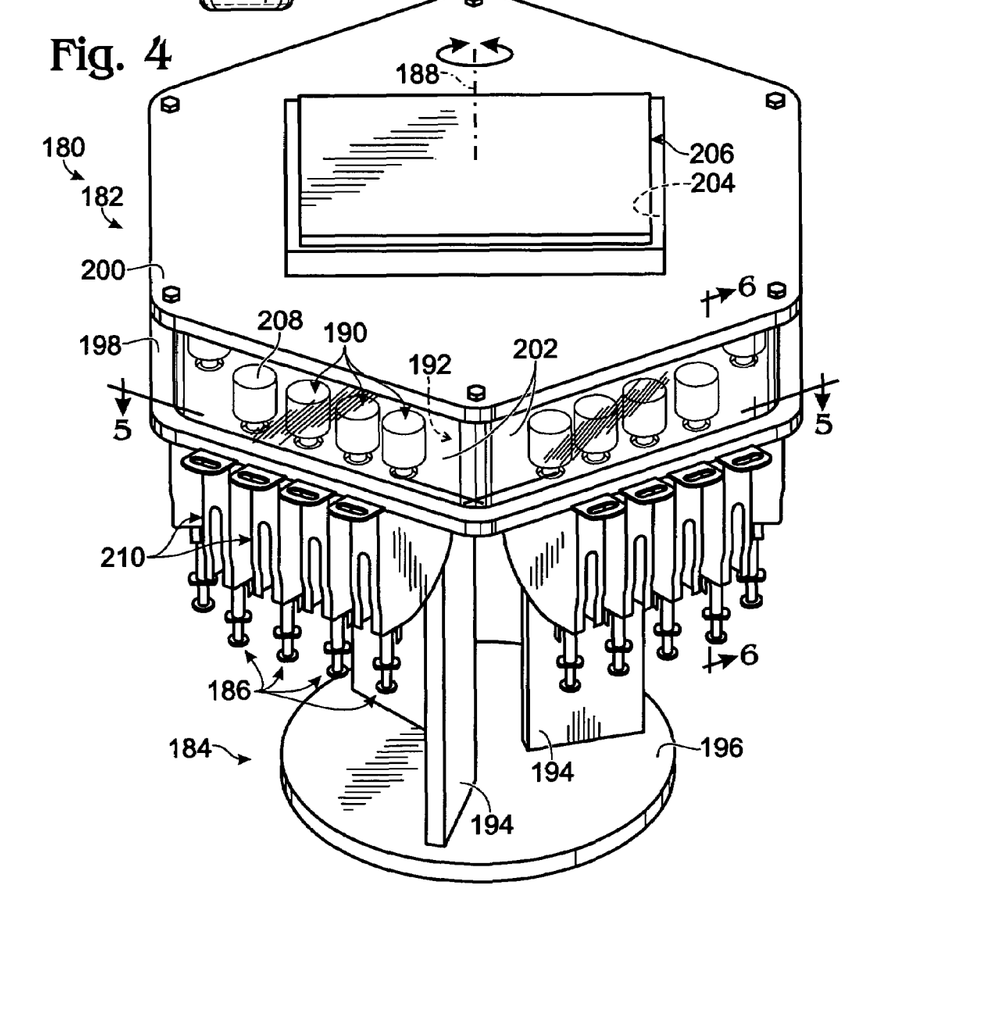
FIG. 4 is a perspective view of an example of an apparatus for dispensing measured volumes of biological fluids under sterile conditions, in accordance with aspects of the present teachings.

The housing 182 may include an opening 204 formed in top wall 200. The opening may be sized to receive a cooling device 206, such as a thermoelectric cooler operating by the Peltier effect. The cooling device may be configured to refrigerate the interior compartment 192 and the allergen stocks 190 housed in this compartment. In some examples, the cooling device may be disposed inside the housing or disposed exterior to, and/or spaced from, the housing. If exterior to the housing, the cooling device may be connected to the housing by one or more ducts.

Each dispenser station 186 may include a stock vial 208 holding an allergen stock 190 (or a vessel holding another fluid, such as a diluent, excipient, drug, etc.). The stock vial may be disposed in an upright or inverted configuration, among others, in the dispenser station. In the present illustration, the stock vials are inverted.

Each dispenser station 186 also may include a dispenser unit 210 attached to the housing and connected to a stock vial. The dispenser unit may be mounted to the bottom wall of the housing. Alternatively, or in addition, the dispenser unit may be mounted to a side wall(s) and/or the top wall.

Figure 5:
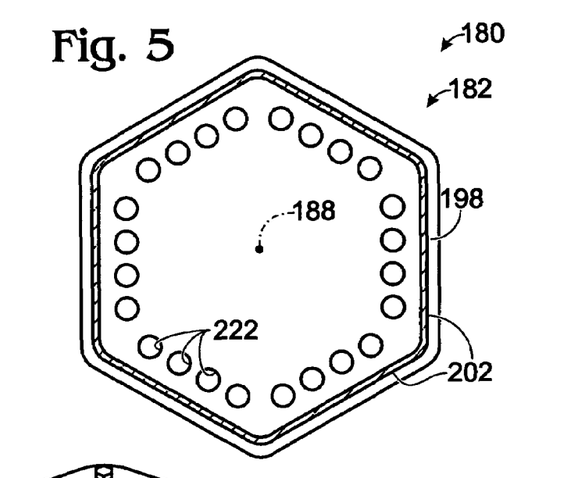
FIG. 5 is a sectional view of the apparatus of FIG. 4, taken generally along line 5-5 of FIG. 4, in the absence of supply vials.

FIG. 5 shows a sectional view of apparatus 180, taken generally along line 5-5 of FIG. 4, in the absence of stock vials and their allergen contents. Housing 182 may include a plurality of apertures 222 formed in the bottom wall 198 of the housing. Each aperture may be configured to receive a stock vial and/or a portion (or all) of a dispenser unit 210. In some examples, the housing may be configured to receive the stock vial and/or dispenser unit from underneath the housing. Alternatively, the stock vial (and/or the dispenser unit) may be placed into (or through) the housing from above the bottom wall, such as through the large opening 204 in the top wall or through a door and/or opening formed in a side wall.

Apertures 222 may be disposed generally around the pivot axis 188 of the housing, inward of the side walls and generally adjacent the perimeter of the bottom wall. Accordingly, the apertures may be disposed in a circular pattern, in a polygonal pattern (angularly disposed sets of rows, such as the hexagonal pattern in the present illustration), in a single row or a set of parallel rows, and/or the like.

Figures 6, 7, 8:
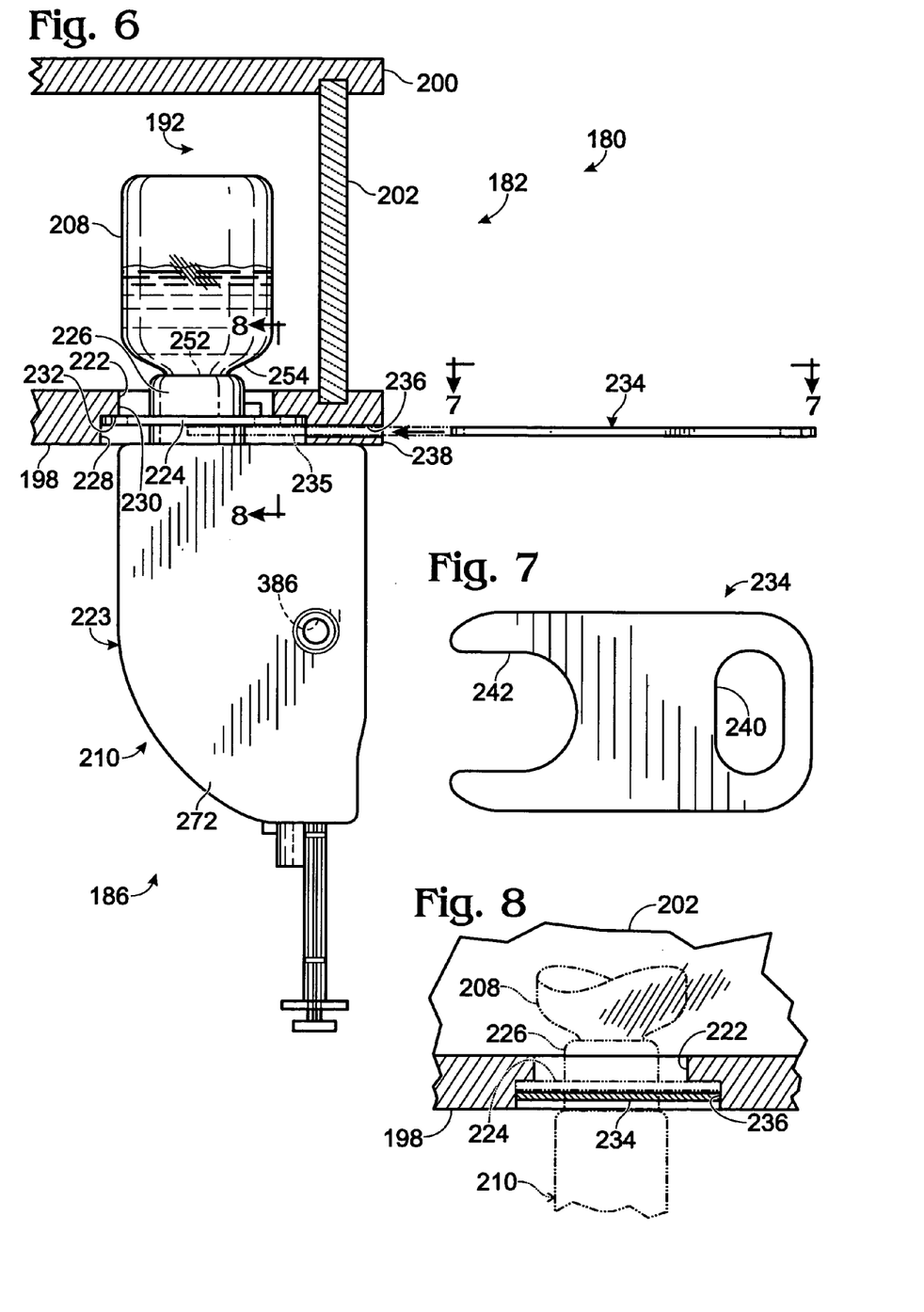
FIG. 6 is a partially exploded, fragmentary sectional view of the apparatus of FIG. 4, taken generally along line 6-6 of FIG. 4.
FIG. 7 is a top plan view of a dispenser retainer of the apparatus of FIG. 4, taken generally along line 7-7 of FIG. 6.
FIG. 8 is fragmentary sectional view of selected portions of the apparatus of FIG. 4, taken generally along line 8-8 of FIG. 6.

FIG. 6 shows a partially exploded, sectional view of selected portions of the dispensing apparatus 180, taken generally along line 6-6 of FIG. 4. An upper portion of the dispenser unit 210 may be received in an aperture 222 formed in the bottom wall 198 of the housing. Stock vial 208 thus may be disposed in the interior compartment 192 of the housing 182. In particular, the dispenser unit 222 may include a frame 223 (the dispenser housing) having a collar or flange 224 extending from a neck portion 226 of the frame. The flange may be received in a lower counterbore 228 of the aperture 222 that is widened relative to an upper bore 230 of the aperture. The flange may engage a shoulder 232 formed at the junction of the bore and counter, to restrict upward movement of the dispenser unit. In some examples, the lower counterbore may be sized and shaped so the flange 224 fits closely into the lower counterbore, so that lateral movement of the flange (and the dispenser unit) is restricted (see FIGS. 6 and 8).

The dispenser unit 210 may be secured to the housing 182 with a retainer 234. The retainer may be received, shown in phantom outline at 235, in a slot 236 formed in the bottom wall 198 of the housing and accessible from the perimeter of the bottom wall. The slot 236 may be sized and positioned so the retainer 234 may slide into the slot and under flange 224 of the dispenser unit. Downward movement of the flange (and the dispenser unit) thus may be restricted by engagement of the flange with the retainer. A lip 238 formed adjacent the slot 236 may restrict downward motion of the retainer 234.

FIG. 7 shows a top plan view of the retainer 234, taken generally along line 7-7 of FIG. 6. The retainer may be generally planar with an aperture 240 that may be engaged with a hand for insertion or removal of the retainer. The retainer also may include a distal opening 242 configured to extend around the neck portion 226 of the dispenser unit, below the flange 224 (see FIGS. 6 and 8).

FIG. 8 shows a sectional view of the dispensing apparatus, taken generally along line 8-8 of FIG. 6, with the retainer fully inserted into the slot 236. Stock vial 208 and dispenser unit 210 are shown in phantom outline to simplify the presentation.

Figure 9:
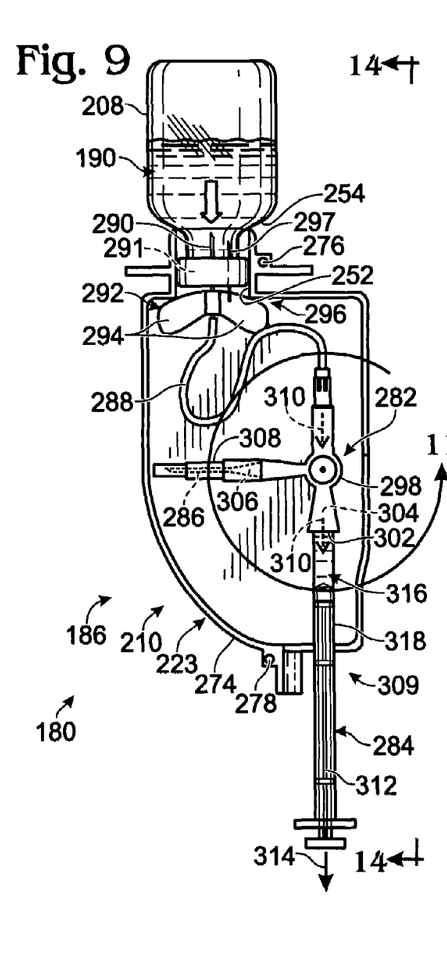
FIG. 9 is a side elevation view of a dispenser station of the apparatus of FIG. 4, viewed generally as in FIG. 6, with the dispenser station in a loading configuration and with a portion of a housing of the dispenser station removed, in accordance with aspects of the present teachings.

FIG. 6 shows the neck portion 226 of the dispenser unit may define an opening 252 in which the neck of the stock vial may be received (see FIG. 9 also). A shoulder 254 formed on the body of the stock vial may engage a rim of the neck portion 226 of the dispenser so that the stock vial may be supported by and rest on the dispenser unit, for example, in the inverted configuration shown in the present illustration. As a result, the allergen stock disposed in the stock vial may be positioned adjacent the closure of the stock vial, which may permit a greater proportion of the allergen stock to be dispensed from the stock vial.

FIG. 9 shows the dispenser station 186 of the dispenser apparatus 180 with a portion of the frame 223 of the dispenser unit 210 removed. Frame 223 may be formed from a single piece or material, or from two or more pieces. In the present illustration, frame 223 includes left-side and right-side components 272, 274. The left-side component 272 is visible in FIG. 6, and the right-side component 274 is shown in FIG. 9. The left-side and right-side components may fit together, for example, with integral pins 276, 278 of the right-side component 274 received in corresponding sockets formed in the left-side component. The left-side and right-side components, when fitted together, may define a shell or dispenser housing that substantially encloses other components of the dispenser unit 210.

The dispenser unit 210 may include a valve 282, a syringe 284, and a delivery needle 286. Valve 282 may be configured to provide adjustable fluid communication between the stock vial 208, the syringe 284, and the delivery needle 286. The valve may be a stock cock valve, among others.

The valve may be connected to the stock vial with a flexible conduit 288 secured to a hollow needle 290. The hollow needle 290 may extend through a septum 291 of the stock vial, to place the fluid contents of the stock vial in fluid communication with the valve 282. The flexible conduit 288 and/or the hollow needle 290 may be attached to a vial retainer 292, configured, for example, with a pair of wings 294. The wings 294 may be long enough that they cannot pass easily through the opening 252 of the neck portion, shown at 296. Accordingly, the vial retainer may help to hold the stock vial in the opening 252 of the neck portion and/or to hold the flexible conduit 288 inside the frame 223 of the dispenser unit. A vent tube 297, such as a hollow needle of small diameter, also may be placed through the septum 291 of the stock vial. The vent tube may function to permit passage of gas into/out of the stock vial, but to restrict passage of liquid out of the stock vial through the vent tube 297.

The valve 282 may be coupled to the syringe 284 by any suitable mechanism. For example, the syringe may be connected to the valve by a flexible conduit. Alternatively, the valve may form a rigid connection with the valve. In the present illustration, the valve housing 298 may form a socket 302 in which a tip 304 of the syringe may be received. The socket 302 and/or the tip 304 may be tapered to facilitate forming a seal between the valve housing and the syringe tip, and/or to permit the syringe to be mated with the housing removably. Alternatively, the syringe may be connected to the housing by, for example, a threaded and/or a Luer-lock coupling.

The valve may be coupled to the delivery needle 286 by a rigid or flexible connection. For example, in the present illustration, a base 306 of the delivery needle 286 may be secured to the valve housing 298, so that the disposition of the delivery needle may be defined by the disposition of the valve housing. Delivery needle 286 may be protected by a sheath or sleeve 308 that reduces exposure of the exterior of the needle to contact with air, liquid, or solid structures, and thus to potential contamination. The sheath or sleeve may be resilient, so that the sheath can be retracted to expose the distal end of the needle. Alternatively, the sheath may be segmented so that it can telescope to expose the distal end of the needle.

Syringe 284 may be disposed in a loading configuration, shown at 309. In this loading configuration, the syringe may be disposed vertically to provide fluid communication between the stock vial and the syringe, indicated by arrows 310. In this loading configuration, the delivery needle 286 may be out of fluid communication with both the syringe and the stock vial, so that fluid from the stock vial cannot pass directly to the delivery needle. Furthermore, the delivery needle may be substantially inaccessible within the frame 223 of the dispenser unit 210. In the loading configuration, a plunger 312 of the syringe may be drawn outward, indicated at 314, to pull a measured volume 316 of the allergen stock 190 into the barrel 318 of the syringe.

Figures 10, 13:
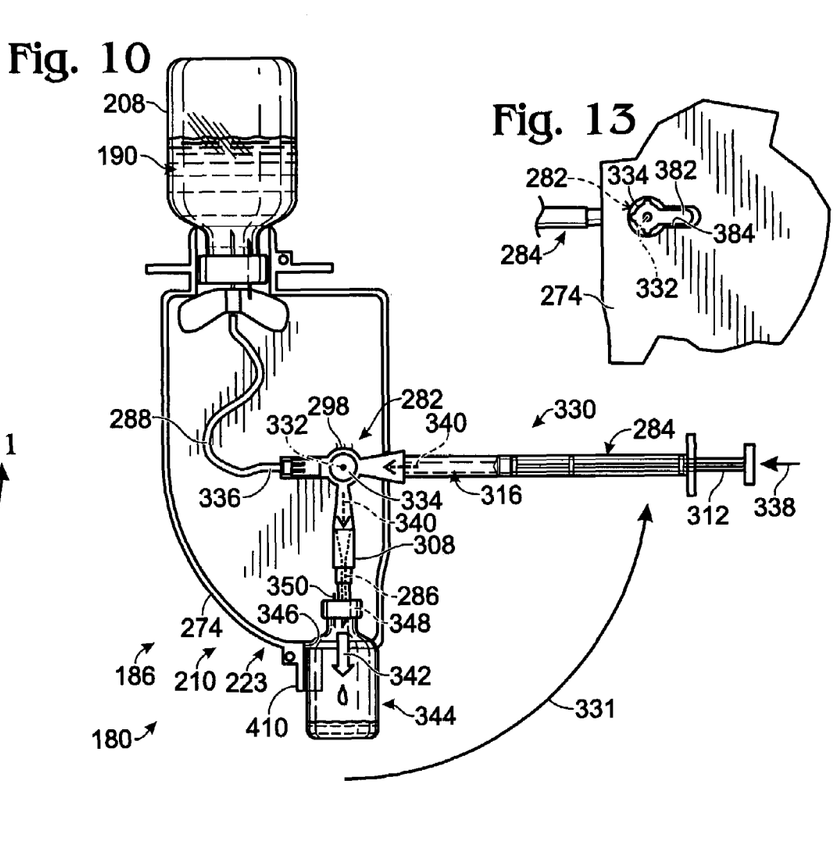
FIG. 10 is a side elevation view of a dispenser station of the apparatus of FIG. 4, viewed generally as in FIG. 6, with the dispenser station in a delivery configuration and with a portion of a housing of the dispenser station removed, in accordance with aspects of the present teachings.
FIG. 13 is fragmentary view of selected portions of the dispenser station of FIG. 10, particularly a valve of the dispenser station, taken generally as in FIG. 12 but from an opposing (exterior) side of the housing.

FIG. 10 shows the dispenser station 186 of the dispenser apparatus 180 in a delivery configuration, indicated at 330. To achieve this configuration, the syringe 284 may be engaged manually and pulled and/or pushed from its vertical loading configuration 309 (see FIG. 9) to a more horizontal position (or from a horizontal to vertical position, or between any other suitable dispositions). The syringe may be rigidly connected to the valve housing 298. Accordingly, turning the syringe (by orbital movement in the present illustration), indicated at 331 in FIG. 10, may produce coupled pivoting of the valve housing about an axis 332 defined by a stem or core 334 of the valve. Accordingly, the syringe, extending radially from the pivot axis 332, may act as a handle and/or lever to pivot the valve housing and thus operate the valve. In particular, pivoting of the valve housing 298 may reposition structures connected to the valve housing, such as a proximal end 336 of the flexible conduit 288 and/or the delivery needle 286 and its associated sheath 308.

Movement of the syringe 284 to the delivery position may create fluid communication between the syringe 284 and the delivery needle 286. Accordingly, the plunger 312 may be pushed into the barrel, shown at 338, to cause the measured volume 316 of fluid to flow along a path, indicated by arrows 340, from the syringe and out of the end of the delivery needle 286, shown at 342. Prior to release of the measured volume of fluid from the syringe, a patient's vial 344 may be received through an opening 346 formed in the frame 223, and into engagement with the delivery needle 286. In particular, a septum 348 of the patient's vial may be penetrated by the tip of the delivery needle, as the sheath 308 is retracted by engagement with the septum (as the vial is moved upward). Delivery of the allergen stock from the syringe to the patient's vial may be facilitated by a vent needle 350 placed through the septum 348 of the patient's vial. The vent needle may function as described above for the vent tube of the stock vial.

Figure 11:
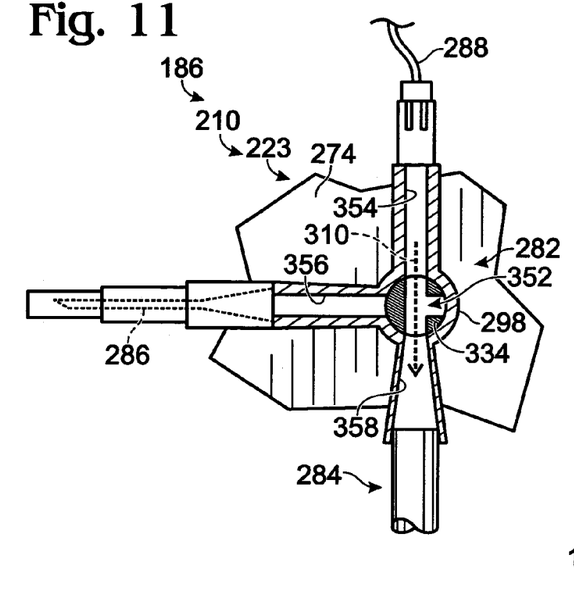
FIG. 11 is a fragmentary view of selected portions of the dispenser station of FIG. 9, particularly a valve of the dispenser station, taken generally at "11" in FIG. 9.
Figure 12:
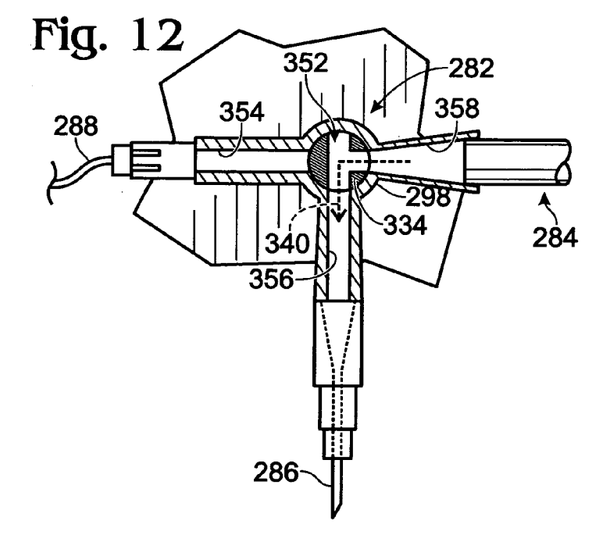
FIG. 12 is a fragmentary view of selected portions of the dispenser station of FIG. 10, particularly a valve of the dispenser station, taken generally as in FIG. 11.

FIGS. 11 and 12 shows fragmentary views of selected portions of the dispenser station 186 of FIG. 9. In particular, these figures show operation of the valve 282 of the dispenser station, viewed from a region labeled "11" in FIG. 9 for FIG. 11 (or a corresponding (unlabeled) region of FIG. 10 for the view of FIG. 12). Valve stem 334 of the valve may include a branched passage 352 (T-shaped in the present illustration) extending from a plurality of positions disposed around the perimeter of the stem. As described in more detail below in relation to FIG. 13, the passage 352 may be fixed in position, so that pairs of conduits 354, 356, 358 of the valve housing may be placed selectively in fluid communication with the passage 352 by pivoting this housing.

FIG. 11 shows the valve housing 298 in the loading configuration. Conduit 354 (connected to the stock vial via tubing 288) and conduit 358 (connected to the syringe 284) may be fluid communication with the passage 352. However, conduit 356 (connected to the delivery needle 286) may be out of fluid communication with this passage (and thus the other conduits 354, 358). Operation of the syringe 284 in this configuration may produce fluid flow along path 310 between the stock vial and the syringe 284, to load the syringe.

FIG. 12 shows the valve housing 298 in the delivery configuration. Conduits 356 and 358 may be in fluid communication with passageway 352, so that fluid can flow along path 340 from the syringe to the delivery needle 286. Conduit 354 may be out of fluid communication in this configuration, to restrict a direct flow of fluid between the stock vial and the delivery needle.

FIG. 13 shows a fragmentary portion of the dispenser station, as in FIG. 12, but from an opposing side of the dispenser unit 210, with the exterior surface of right-side component 274 visible. The valve stem 334 may be substantially fixed in position (restricted from pivoting and/or translational motion) by engagement of the stem with the frame of the dispenser unit. In particular, the stem may include a projection, such as a flange or handle 382, that is received by a receiver structure or opening 384 formed in the right-side component 274 of the frame. The handle 382 may extend radially from the pivot axis 332 of the stem. Alternatively, the frame 223 may include a projection received by the stem to restrict pivoting of the stem. The left-side component of the frame also may engage the valve to prevent the valve from sliding or wobbling in the frame. For example, FIG. 8 shows an opening 386 defined by the left-side component 272 that receives an opposing side of the valve.

In some embodiments, handle 382 of the stem 334 may be operable manually. Accordingly, the dispenser station may be switchable between loading and delivery configurations by operating the handle through manual engagement of this handle. However, pivoting the valve housing through movement of the syringe, rather than pivoting the stem with direct engagement of the handle 382, may offer advantages over movement of the handle. In particular, the syringe may provide a mechanical advantage through a longer lever arm (to exert greater torque). Alternatively, or in addition, use of the syringe as a lever may provide a visual indication of individual steps of the dispensing process, based on the position of the syringe. The rate of dispensing errors thus may be reduced.

Figure 14:
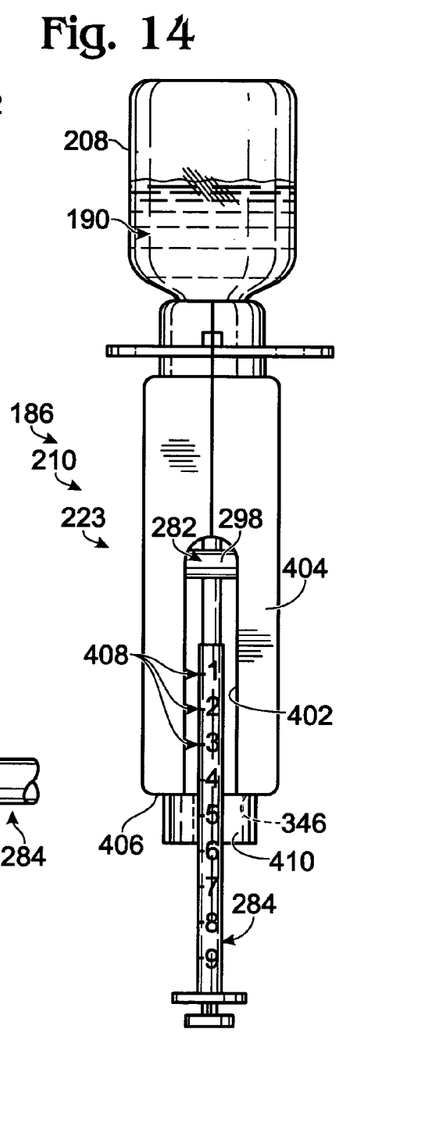
FIG. 14 is a side elevation view from the front of the dispenser station of FIG. 9, taken generally along line 14-14 of FIG. 9 with the housing assembled.

FIG. 14 shows the dispenser station 186 viewed generally along line 14-14 of FIG. 9, but with the frame 223 assembled. Frame 223 may define an elongate opening 402 extending formed vertically in a front wall 404 of the frame. The vertical opening 402 may permit the syringe to move orbitally (compare FIGS. 9 and 10), as the valve housing 298 pivots. Accordingly, the opening 402 may extend from a bottom wall 406 to a vertical position slightly above the valve 282. Opening 402 also may permit indicia 408 (such as graduations and/or numbers, among others) to be visible as fluid is loaded into the syringe. (In the present illustration, the numbers may represent tenths of milliliters.) The indicia may be configured to permit a measured volume of a biological fluid to be loaded into the syringe and/or to be released from the syringe into a receiver vial.

Vertical opening 402 may adjoin a horizontal opening 346 formed in the bottom wall 406. The horizontal or bottom opening 346 may be wider than vertical opening 402, to permit a patient's vial to be received selectively in the bottom opening (also see FIG. 10).

FIG. 14 shows the frame also may include a guide 410 disposed adjacent the bottom opening 346. Guide 410 may be configured to guide the patient's vial into the bottom opening, for engagement with the delivery needle (see also FIG. 10). Accordingly, the guide may be arcuate in shape to generally match a cylindrical contour of the patient's vial.

The disclosure set forth above may encompass one or more distinct inventions, with independent utility. Each of these inventions has been disclosed in its preferred form(s). These preferred forms, including the specific embodiments thereof as disclosed and illustrated herein, are not intended to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

I claim:

1. A method of dispensing biological fluids, comprising:

disposing a plurality of sealed stock vials in a housing to form an array, the stock vials holding biological fluids and each being disposed in an inverted configuration;

operating at least one cooling device to refrigerate the stock vials with the stock vials disposed in the housing; and transferring aliquots of the biological fluids using syringe pumps such that the aliquots are transferred from two or more of the stock vials disposed in the inverted configuration in the housing, out through resilient closures of the two or more stock vials, and to a receiver vial through a resilient closure thereof.

2. The method of claim 1, wherein the step of disposing includes a step of disposing each stock vial such that a resilient closure of the stock vial is disposed below a sterile biological fluid contained by the stock vial.

3. The method of claim 1, wherein the step of disposing includes a step of disposing stock vials holding allergens, and wherein the step of transferring includes a step of transferring aliquots of two or more of the allergens to form an allergen mixture in the receiver vial for an allergy patient.

4. The method of claim 1, wherein the step of disposing includes a step of disposing stock vials in a housing that is generally circular.

5. The method of claim 1, wherein the step of disposing includes a step of disposing the stock vials inside a housing having a transparent wall.

6. The method of claim 1, wherein the step of operating at least one cooling device includes a step of operating at least one thermoelectric cooling device.

7. The method of claim 6, further comprising a step of sensing a temperature of the housing, and wherein the step of operating at least one thermoelectric cooling device is based on the step of sensing a temperature.

8. The method of claim 7, wherein the step of sensing is performed with one or more sensors in communication with a controller, further comprising a step of maintaining a record of temperatures sensed by the sensors in memory of the controller.

9. The method of claim 1, wherein the housing is connected to a base, further comprising a step of rotating the array of stock vials relative to the base in order to select at least one stock vial from which an aliquot is to be transferred.

10. The method of claim 9, wherein the step of disposing includes a step of disposing the stock vials in a circular pattern around a pivot axis, and wherein the step of rotating includes a step of rotating at least a portion of the housing about the pivot axis.

11. The method of claim 1, further comprising a step of penetrating the resilient closures of the two or more stock vials and the resilient closure of the receiver vial with hollow-bore needles coupled to the syringe pumps, wherein the step of transferring includes a step of moving the aliquots through the hollow-bore needles.

12. The method of claim 1, wherein the step of transferring includes a step of transferring aliquots using power-driven syringe pumps.

13. The method of claim 12, where the step of transferring includes a step of automatically operating the power-driven syringe pumps.

14. The method of claim 1, wherein the step of transferring includes a step of sensing positions of the syringe pumps via one or more sensors, and a step of manipulating data corresponding to the sensed positions with a controller.

15. The method of claim 1, further comprising a step of inputting instructions for the step of transferring to a controller that controls operation of the syringe pumps.

16. The method of claim 15, wherein the step of inputting instructions includes a step of inputting instructions to the controller via a touchscreen.

17. The method of claim 1, further comprising a step of maintaining a record of aspects of the step of transferring in memory of a controller.

18. A system for dispensing biological fluids, comprising:

a housing for holding an array of sealed stock vials containing biological fluids, with each stock vial being disposed in an inverted configuration;

at least one cooling device operatively coupled to the housing and configured to refrigerate the stock vials with the stock vials disposed in the housing; and a plurality of syringe pumps for transferring aliquots of the biological fluids from the stock vials disposed in the inverted configuration in the housing, out through resilient closures of the stock vials, each syringe pump being coupled to a hollow-bore needle, wherein the housing is configured to hold the stock vials such that the resilient closures are accessible to the hollow-bore needles from below the stock vials.

19. The system of claim 18, wherein the housing is generally circular.

20. The system of claim 18, wherein the housing includes a transparent wall.

21. The system of claim 18, where the at least one cooling device is a thermoelectric cooling device.

22. The system of claim 18, further comprising one or more sensors operatively coupled to the housing and configured to sense a temperature of the housing.

23. The system of claim 22, further comprising a controller in communication with the one or more sensors and configured to operate the at least one cooling device based on data from the one or more sensors.

24. The system of claim 22, further comprising a controller in communication with the one or more sensors and configured to maintain a record of temperatures sensed by the sensors in memory of the controller.

25. The system of claim 18, wherein the housing is connected to a base such that the array of stock vials can be rotated relative to the base in order to select a stock vial from which an aliquot is to be transferred.

26. The system of claim 18, wherein the housing is configured to dispose the stock vials in a circular pattern around a pivot axis such that the array of stock vials can be rotated about the pivot axis.

27. The system of claim 18, wherein the housing has a polygonal shape.

28. The system of claim 18, wherein the syringe pumps are power-driven syringe pumps.

29. The system of claim 28, further comprising a controller operatively coupled to the power-driven syringe pumps for automatic operation thereof.

30. The system of claim 29, further comprising one or more sensors in communication with the controller and configured to sense positions of the syringe pumps.

31. The system of claim 29, wherein the controller includes a user interface for inputting instructions about dispensing the biological fluids.

32. The system of claim 31, wherein the user interface includes a touchscreen.

33. The system of claim 31, wherein the controller is configured to a maintain a record of aspects of dispensing in memory of the controller.

34. A method of dispensing biological fluids, comprising:
disposing a plurality of sealed stock vials in a housing in a circular pattern to form an array, the stock vials holding biological fluids and each being disposed in an inverted configuration;
operating at least one thermoelectric cooling device to refrigerate the stock vials with the stock vials disposed in the housing; and
transferring aliquots of the biological fluids using syringe pumps such that the aliquots are transferred from two or more of the stock vials disposed in the inverted configuration in the housing, out through resilient closures of the two or more stock vials, and to a receiver vial through a resilient closure thereof.

* * * * *